(12) United States Patent
Fritz

(10) Patent No.: US 6,700,130 B2
(45) Date of Patent: Mar. 2, 2004

(54) OPTICAL DETECTION SYSTEM FOR FLOW CYTOMETRY

(75) Inventor: Bernard Steven Fritz, Eagan, MN (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 09/896,230

(22) Filed: Jun. 29, 2001

(65) Prior Publication Data

US 2003/0002027 A1 Jan. 2, 2003

(51) Int. Cl.$^7$ ................................................. G01N 15/06
(52) U.S. Cl. ........................................ 250/573; 356/436
(58) Field of Search ........................ 356/436, 39, 440, 356/335, 336, 441, 442; 422/82.09; 250/573, 574, 578.1, 436

(56) References Cited

U.S. PATENT DOCUMENTS

| | | | | |
|---|---|---|---|---|
| 3,822,095 A | * | 7/1974 | Hirschfeld | 356/39 |
| 4,478,076 A | | 10/1984 | Bohrer | 73/204 |
| 4,478,077 A | | 10/1984 | Boher | 73/204 |

(List continued on next page.)

OTHER PUBLICATIONS

U.S. patent application Ser. No. 09/630,927, Cabuz et al., filed Aug. 2, 2000.
http://www.micronics.net/tsensor.htm, pp. 1–4, downloaded Jun. 14, 2000.
http://www.micronics.net/hfilter.htm, pp. 1–3, downloaded Jun. 14, 2000.
http://www.micronics.net/mcytometry.htm, pp. 1–4, downloaded Jun. 14, 2000.
http://www.micronics.net/orcafluidics.htm, pp. 1–4, downloaded Jun. 14, 2000.
Shapiro, "Practical Flow Cytometry", third edition, 1995, p. 237.
T. Ohnstein et al., "Micromachined Silicon Microvalve", Proceedings of MEMS, 1990, IEEE Micro Electromechanical Systems, Napa Valley, California, Feb. 11–14, 1990, pp. 95–98.
Strzelecka, E. et al., "Parallel Free–Space Optical Interconnect Based on Arrays of Vertical–Cavity Lasers and Detectors with Monolithic Microlenses", Applied Optics, v. 37(14), May 10, 1998, pp. 2811–2821, Copyright 1998 Optical Society of America.
Lehman, J. et al., "High–Frequency Modulation Characteristics of Red VCSELs", Electronics Letters, Feb. 13, 1997, vol. 33(4), pp. 298–300. Copyright 1997 IEE.

(List continued on next page.)

Primary Examiner—Que T. Le
Assistant Examiner—Eric Spears
(74) Attorney, Agent, or Firm—Kris T. Fredrick

(57) ABSTRACT

An optical detection system for flow cytometry that uses two or more light sources positioned laterally at different distances from a central axis of a flow stream for providing light through different parts of the flow stream. One or more lenses are used to focus the light from the two or more light sources through the flow stream and onto a common focal point or region on the opposite side of the flow stream. One or more light detectors are then placed at, near or around the common focal point or region. A processor or the like receives at least one output signal from the one or more light detectors to analyze and determine selected characteristics of the flow stream.

38 Claims, 10 Drawing Sheets

U.S. PATENT DOCUMENTS

| | | | | |
|---|---|---|---|---|
| 4,501,144 A | | 2/1985 | Higashi et al. | 73/204 |
| 4,651,564 A | | 3/1987 | Johnson et al. | 73/204 |
| 4,683,159 A | | 7/1987 | Bohrer et al. | 428/138 |
| 5,050,429 A | | 9/1991 | Nishimoto et al. | 73/204.26 |
| 5,082,242 A | | 1/1992 | Bonne et al. | 251/129.01 |
| 5,108,623 A | | 4/1992 | Cangelosi et al. | 210/744 |
| 5,176,358 A | | 1/1993 | Bonne et al. | 251/30.05 |
| 5,194,909 A | * | 3/1993 | Tycko | 356/40 |
| 5,241,368 A | * | 8/1993 | Ponstingl et al. | 356/436 |
| 5,244,537 A | | 9/1993 | Ohnstein | 156/643 |
| 5,323,999 A | | 6/1994 | Bonne et al. | 251/11 |
| 5,441,597 A | | 8/1995 | Bonne et al. | 216/2 |
| 5,444,530 A | * | 8/1995 | Wang | 356/338 |
| 5,570,193 A | * | 10/1996 | Landa et al. | 356/442 |
| 5,616,501 A | * | 4/1997 | Rodriguez et al. | 436/63 |
| 5,716,852 A | | 2/1998 | Yager et al. | 436/172 |
| 5,726,751 A | | 3/1998 | Altendorf et al. | 356/246 |
| 5,737,078 A | * | 4/1998 | Takarada et al. | 356/338 |
| 5,799,030 A | | 8/1998 | Brenner | 372/50 |
| 5,822,170 A | | 10/1998 | Cabuz et al. | 361/225 |
| 5,836,750 A | | 11/1998 | Cabuz | 417/322 |
| 5,893,722 A | | 4/1999 | Hibbs-Brenner et al. | 438/45 |
| 5,922,210 A | | 7/1999 | Brody et al. | 210/767 |
| 5,932,100 A | | 8/1999 | Yager et al. | 210/634 |
| 5,948,684 A | | 9/1999 | Weigl et al. | 436/52 |
| 5,971,158 A | | 10/1999 | Yager et al. | 209/155 |
| 5,972,710 A | | 10/1999 | Weigl et al. | 436/34 |
| 5,974,867 A | | 11/1999 | Forster et al. | 73/61.41 |
| 6,007,775 A | | 12/1999 | Yager | 422/57 |
| 6,008,729 A | * | 12/1999 | Hamburger et al. | 340/627 |
| 6,240,944 B1 | | 6/2001 | Ohnstein et al. | 137/1 |
| 6,281,975 B1 | * | 8/2001 | Munk | 356/440 |
| 6,479,833 B1 | * | 11/2002 | Pfefferseder et al. | 250/573 |

OTHER PUBLICATIONS

"Applying Microfluidic Chemical Analytical Systems To Imperfect Samples", P. Yager et al., Micro Total Analysis Systems 98, D. Harrison & A. van den Berg (ed.), Kluwer Academic Publishers, Dordrecht, 207–212, 1998.

"Design Of Microfluidic Sample Preconditioning Systems For Detection Of Biological Agents In Environmental Samples", Yager, M. et al., SPIE Proceedings, 3515, 252–259, 1998. Abstract.

"Development Of A Flow Cytometry Based Miniature Chemical Fluid Analysis System Using Fluorescent Microbeads", M. Huang. et al., SPIE Biomedical Optics, BIOS 97, conference proceedings, 1997.

"Differential Blood Cell Counts Obtained Using A Microchannel Based Flow Cytometer", E. Altendorf et al., Solid State Sensors & Actuators, vol. 1, 531, 1997.

"Diffusion–Based Optical Chemical Detection In Silicon Flow Structures", B. Weigl et al., Analytical Methods & Instrumentation, μTTAS 96 special edition, 1996.

"Fluorescence And Absorbance Analyte Sensing In Whole Blood And Plasma Based On Diffusion Separation In Silicon–Microfabricated Flow Structures (T–Sensors™)", B. Weigl, et al., Biomedical Optics, vol. 6, No. 1, Jul. 1997.

"Implementation Of Novel Optical Detection Methods For Clinically Important Blood Analytes Using Microfabricated Flow Structures (T–Sensors™)", E. Altendorf & B. Weigl, MicroTAS 98, Banff, Canada, Apr. 1998.

"Integration Of Microelectrodes With Etched Microchannels For In–Stream Electrochemical Analysis", R.Darling et al., MicroTAS 98, Banff, Canada, Apr. 1998.

"Microfabrication Technology For Research And Diagnostics, Silicon Microchannel Optical Flow Cytometry", E. Altendorf et al., SPIE Proceedings, Biomedical Optics 96, Jan. 1996.

"Microfluidic Approaches to Immunoassays", A. Hatch et al., SPIE Conference on Micromachining amd Microfabrication Symposium at Santa Clara, CA, Sep. 20–22, 1999.

"Microfluidic Diffusion Based Electrochemical Detection Using Microfabricated Flow Structures (T–Sensors™)", B. Weigl, Analytical Chemistry, submitted 1999.

"Microfluidic Diffusion–Based Separation And Detection", B. Weigl & P. Yager, Science, Vol 283, pp 346–7, Jan. 15, 1999.

"Optical And Electrochemical Diffusion–Based Detection Of Analytes In Complex Samples Using Microfabricated Flow Structures (T–SensorSTM)", B. Weigl, R. Darling, P. Yager, J. Kriebel & K. Mayes, Micro– and nanofabn'cated electro–optical mechanical systems for biomedical and environmental applications II–SPIE vol. 3606, Jan. 25–26, 1999. Abstract.

"Rapid Sequential Chemical Analysis Using Multiple Fluorescent Reporter Beads", B. Weigl et al., μTTAS 96 Conference Proceedings, 1996.

"Results Obtained Using A Prototype Microfludics–Based Hematology Analyzer", E.Altendorf et al., SPIE Biomedical Optics 97, 1997.

"Silicon–Microfabricated Diffusion–Based Optical Chemical Sensor", B. Weigh & P. Yager, Reprint from "Sensors & Actuators" B 38–39, 452–457, 1997.

"Simultaneous Self–Referencing Analyte Determination In Complex Sample Solutions Using Microfabricated Flow Structures (T–Sensors™)", B. Weigl et al., Proceedings of MicroTAS 98, 81–4, Banff, Canada, 1998.

"Whole Blood Assays Using Microfluidics–Based T–SensorSTm Technology", B. Weigl, Medical Design Online, http://news.medicaldesignonline.com/featuresarticles/19990416–5922.html, Apr. 1999.

Cabuz, et al., "Mesoscopic Sampler Based on 3D Array of Electrostatically Activated Diaphragms", Transducers '99, The 10th International Conference on Solid–State Sensors and Actuators, Digest of Technical Papers, vol. 2, Jun. 7–10, 1999.

Terstappen, et al., "Four–Parameter White Blood Cell Differential Counting Based on Light Scattering Measurements", Alan R. Liss, Inc., Cytometery 9:39–43, 1988.

Eric Alterndorf et al., "Results Obtained Using a Prototype Microfluidics–Based Hematology Analyzer," uTAS 98, D.J. Harrison and A. van den Berg, eds, Kluwer Academic Publishers, Dordrecht, (1998), pp. 73–76.

B. Weigl, et al., "Fluorescence Analyte Sensing In Whole Blood Based On Diffusion Separation In Silicon–Microfabricated Flow Structures," SPIE Proceedings, J. Lakowitz (ed.), Advances in Fluorescence Sensing Technology III, 1997, pp. 171–181.

* cited by examiner

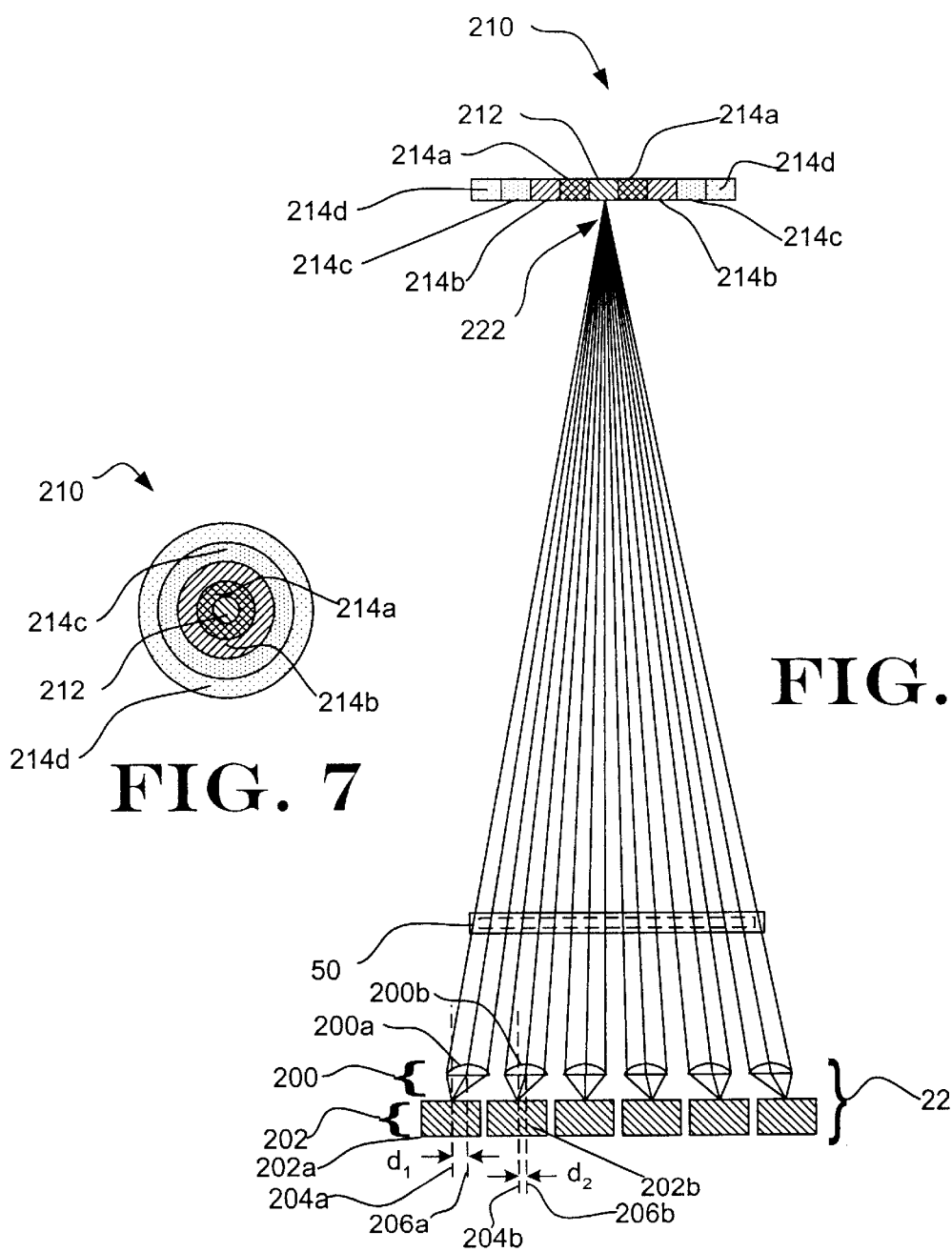

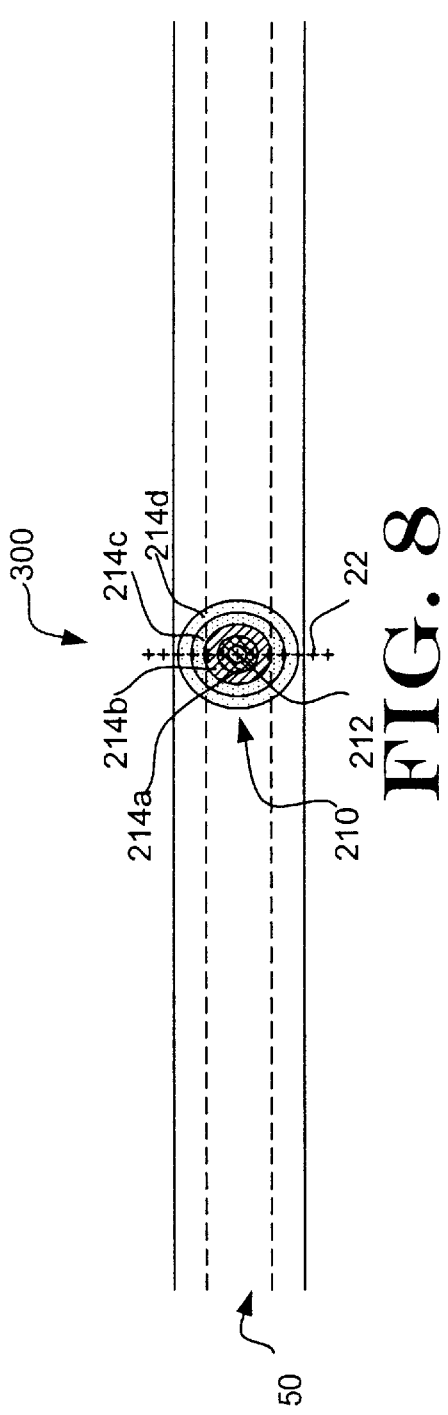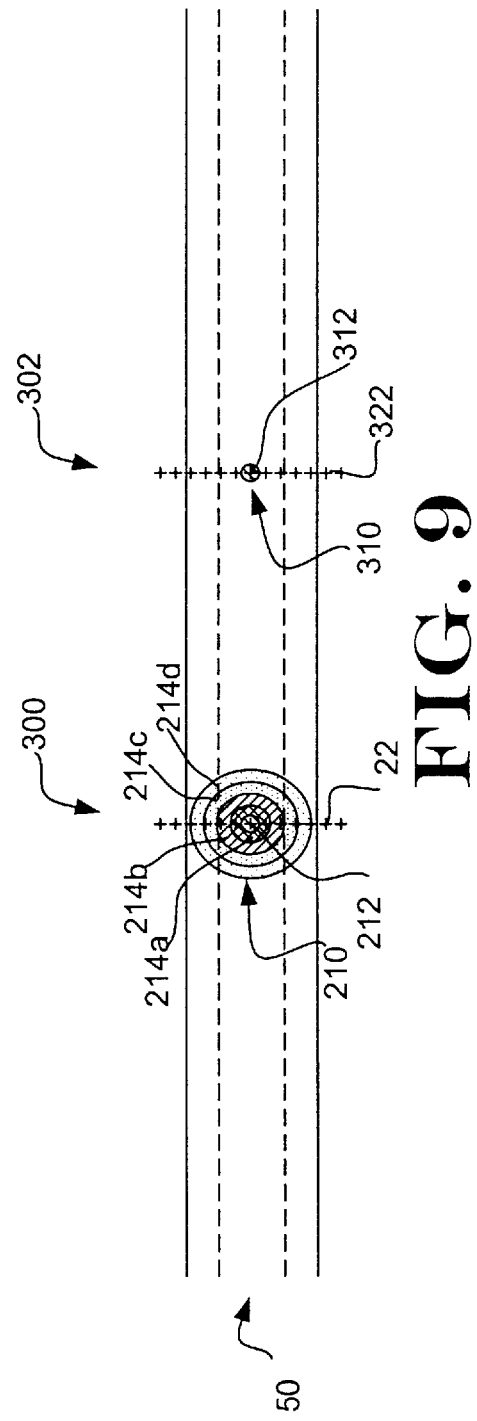

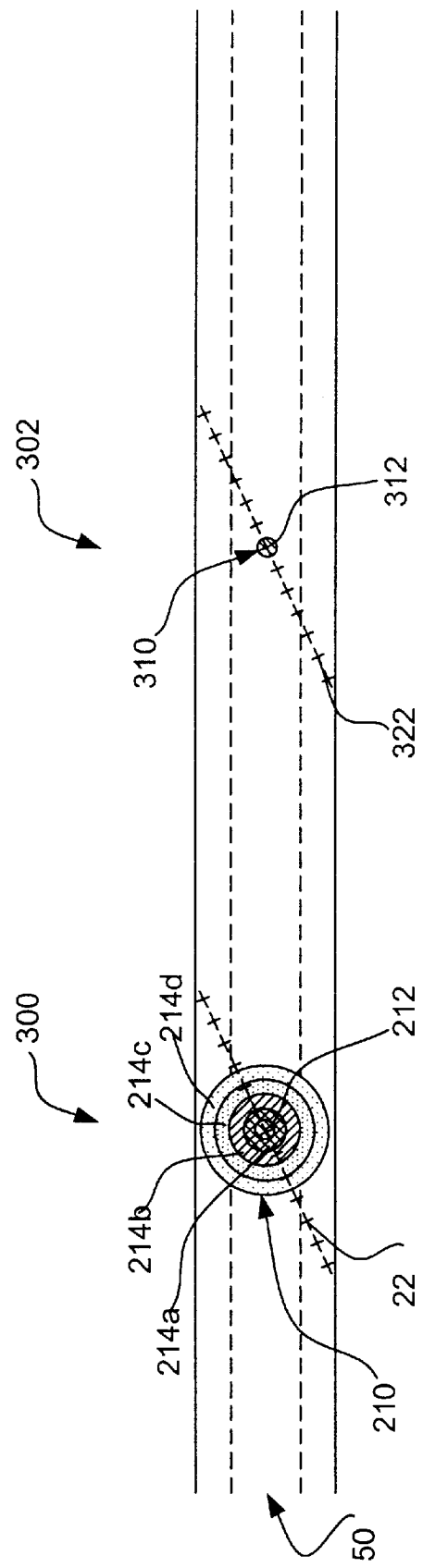

OPTICAL DETECTION SYSTEM FOR FLOW CYTOMETRY

CROSS-REFERENCE TO RELATED CO-PENDING APPLICATIONS

This Application is related to co-pending U.S. patent application Ser. No. 09/630,927 to Cabuz et al., filed Aug. 2, 2000, and entitled "OPTICAL DETECTION SYSTEM FOR FLOW CYTOMETRY", which is incorporated herein by reference.

The Government may have rights in this invention pursuant to Contract No. MDA972-00-C-0029.

FIELD OF THE INVENTION

The present invention relates generally to flow cytometers. More particularly, the present invention relates to optical detection systems for flow cytometer systems.

BACKGROUND OF THE INVENTION

Flow cytometry is a technique that is used to determine certain physical and chemical properties of microscopic biological particles by sensing certain optical properties of the particles. Flow cytometry is currently used in a wide variety of applications including hematology, immunology, genetics, food science, pharmacology, microbiology, parasitology and oncology.

In flow cytometry, the microscopic biological particles of a sample fluid are arranged in single file in a core stream, typically using hydrodynamic focusing. The particles are then individually interrogated by an optical detection system. The optical detection system provides a light beam, which is scattered by each particle to produce a scatter profile. The scatter profile is analyzed by measuring the light intensity at both small and larger scatter angles. Certain physical and/or chemical properties of each particle can then be determined from the scatter profile.

Conventional cytometer systems use a single light source such as a laser to interrogate each particle. The light beam is often focused to an elongated shape that covers the uncertainty in particle position due to misalignment and variations in the width of the core stream. A limitation of using a single light source is that the particle position and variations in the width of the core stream cannot be directly detected. Misalignments in particle position and variations in the width of the core stream can be indicators of improper core formation. Because there may be no direct way of monitoring the characteristics of the core stream, improper core formation may go undetected.

This limitation may be further compounded because the single laser source configuration often does not provide a constant illumination intensity across the flow channel. As such, particles that pass more toward the edge of the core stream may not be as illuminated as particles that pass near the center. As a result, the sensitivity and accuracy of the system may vary depending on the lateral position of the particle through the focused elongated shape beam. Since there may be no easy way of detecting the lateral position of each particle, the variations in sensitivity and accuracy may go undetected.

Another limitation of using a single light source is that the velocity of each particle cannot be directly determined. Particle velocity is often an important parameter in estimating the particle size from light scatter signals. In conventional flow cytometry systems, the velocity of each particle is extrapolated from the pump flow rates. Accordingly, to accurately gauge the velocity of each particle, the pumps must be very precise, the tolerance of the cytometer flow chambers must be tightly controlled, no fluid failures such as leaks can occur, and no obstructions such as microbubbles can be introduced to disturb the flow or core formation. Satisfying these constraints can add significant complexity and cost to the flow cytometer system.

SUMMARY OF THE INVENTION

The present invention overcomes many of the disadvantages of the prior art by providing an optical detection system that uses two or more light sources positioned laterally at different distances from a central axis of a flow stream for providing light through different parts of the flow stream. One or more lenses are used to focus the light from the two or more light sources through the flow stream and onto a common focal point or region on the opposite side of the flow stream. One or more light detectors are then placed at, near or around the common focal point or region. A processor or the like may then receive at least one output signal from the one or more light detectors to analyze and determine selected characteristics of the flow stream.

In one illustrative embodiment of the present invention, an array of light sources and an array of lenses are used to illuminate a flow stream. To focus the light from each of the light sources through the flow stream to a common focal point or region on the opposite side of the flow stream, the pitch of the lens array is slightly different than the pitch of the light source array. This creates an offset between the optical axis of each lens and the corresponding light source, and this offset varies across the arrays. The various offsets are preferably set so that each lens focuses the light from the corresponding light source onto the common focal point or region on the opposite side of the flow stream. A multiple annular zoned detector is then positioned at, near or around the common focal point or region to measure the incident intensity distribution over various angular zone regions.

Blood cells or other particles present in the flow channel tend to diffract or scatter the light out of the central zone of the annular zoned detector and onto outer annular detector zones. Analysis of the signal strength produced by the various annular zones can be used to determine certain physical and/or chemical properties of each particle passing through the flow channel. Such an analysis can be used to determine, for example, if a particle is present in the flow stream, the speed and alignment of the particle within the flow stream, and in many cases, the type of particle.

In one illustrative application, the optical detection system of the present invention may be used in conjunction with a portable cytometer system for detecting, for example, neutrophils and/or lymphocytes white blood cells in a blood sample. By examining the scatter distribution of each of the particles, the portable cytometer may identify and count the neutrophils and lymphocytes in the blood sample, and provide a clear infection warning with differentiation between viral and bacterial causes. Many other applications are also contemplated.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 6 is a schematic diagram showing an array of light sources, an array of lenses and a cross sectional view of an annular zoned detector;

FIG. 7 is an illustrative diagram of a top frontal view of the annular zoned detector of FIG. 6;

FIG. 8 is a schematic diagram showing an array of light sources positioned along an axis that is angularly offset by about ninety degrees relative to the central axis of a flow channel and a single annular zoned detector positioned on the opposite side of the flow stream;

FIG. 9 is a schematic diagram showing two arrays of light sources, each positioned along an axis that is angularly offset by about ninety degrees relative to the central axis of a flow channel, and two annular zoned detectors positioned on the opposite side of the flow stream;

FIG. 10 is a schematic diagram showing two separate arrays of light sources, each positioned along an axis that is angularly offset by less than ninety degrees relative to the central axis of the flow stream, with two annular zoned detectors;

DETAILED DESCRIPTION OF THE PREFERRED EMBODIMENTS

Figure 1:
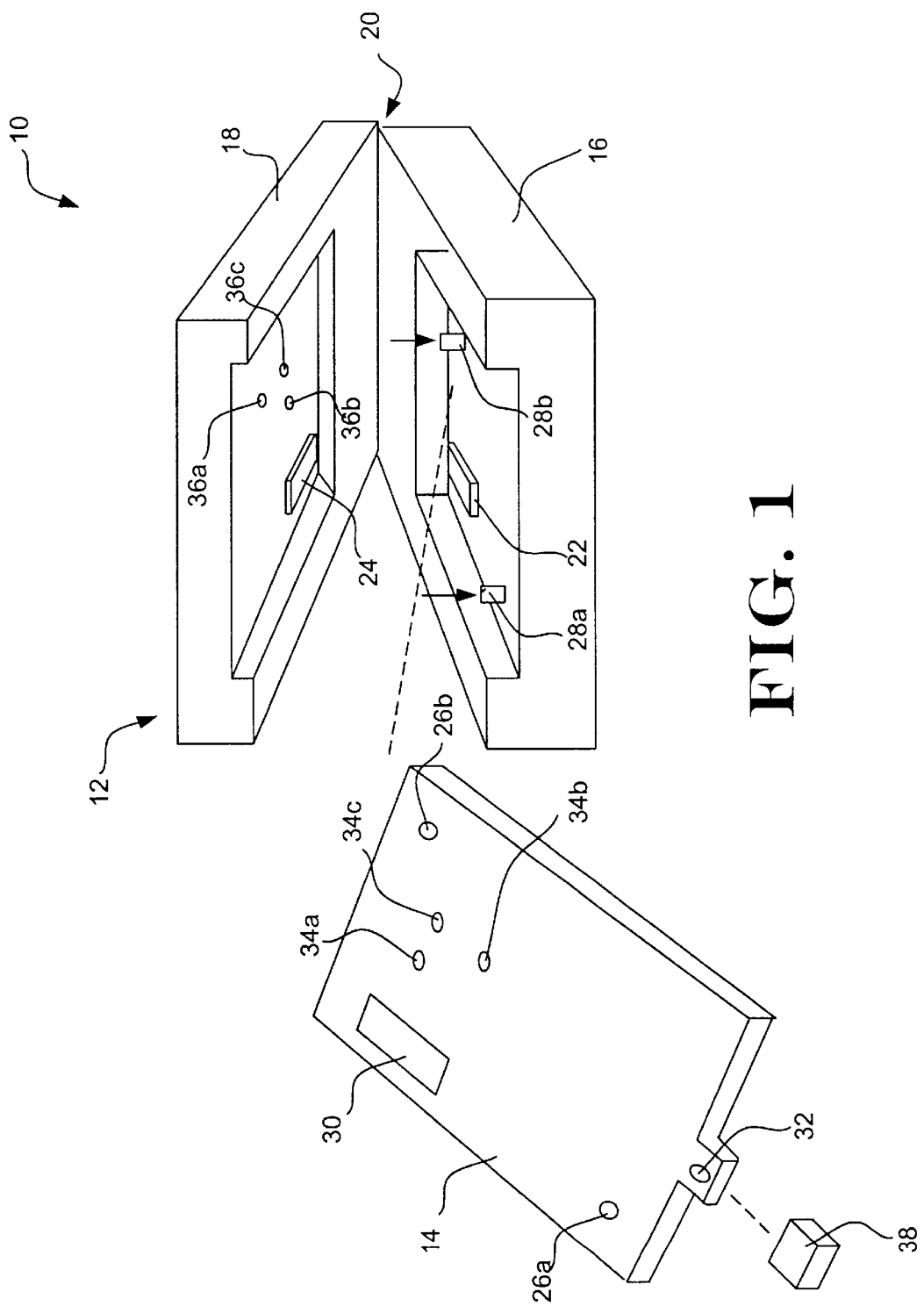
FIG. 1 is a perspective view of an illustrative portable cytometer in accordance with the present invention.

FIG. 1 is a perspective view of an illustrative portable cytometer in accordance with the present invention. The portable cytometer is generally shown at 10, and includes a housing 12 and a removable or replaceable cartridge 14. The illustrative housing 12 includes a base 16, a cover 18, and a hinge 20 that attaches the base 16 to the cover 18. The base 16 includes an array of light sources 22, associated optics and the necessary electronics for operation of the cytometer. The cover 12 includes a manual pressurizing element, pressure-chambers with control microvalves, and an array of light detectors 24.

The removable cartridge 14 preferably receives a sample fluid via a sample collector port 32. A cap 38 may be used to protect the sample collector port 32 when the removable cartridge 14 is not in use. The removable cartridge 14 preferably performs blood dilution, red cell lysing, and hydrodynamic focusing for core formation. The removable cartridge 14 may be constructed similar to the fluidic circuits available from Micronics Technologies, some of which are fabricated using a laminated structure with etched channels.

The removable cartridge 14 is inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also preferably includes a transparent flow stream window 30, which is in alignment with the array of the light sources 22 and light detectors 24. When the cover is moved to the closed position, and the system is pressurized, the cover 18 provides controlled pressures to pressure receiving ports 34a, 34b, and 34c in the removable cartridge 14 via pressure providing ports 36a, 36b and 36c, respectively.

To initiate a test, the cover 18 is lifted and a new cartridge 14 is placed and registered onto the base 16. A blood sample is introduced into the sample collector 32. The cover 18 is closed and the system is manually pressurized. Once pressurized, the instrument performs a white blood cell cytometry measurement. The removable cartridge 14 provides blood dilution, red cell lysing, and hydrodynamic focusing for core formation. The light sources 22, light detectors 24 and associated control and processing electronics perform differentiation and counting of white blood cells based on light scattering signals. Rather than using a hinged construction for the housing 12, it is contemplated that a sliding cartridge slot or any other suitable construction may be used.

Figure 2:
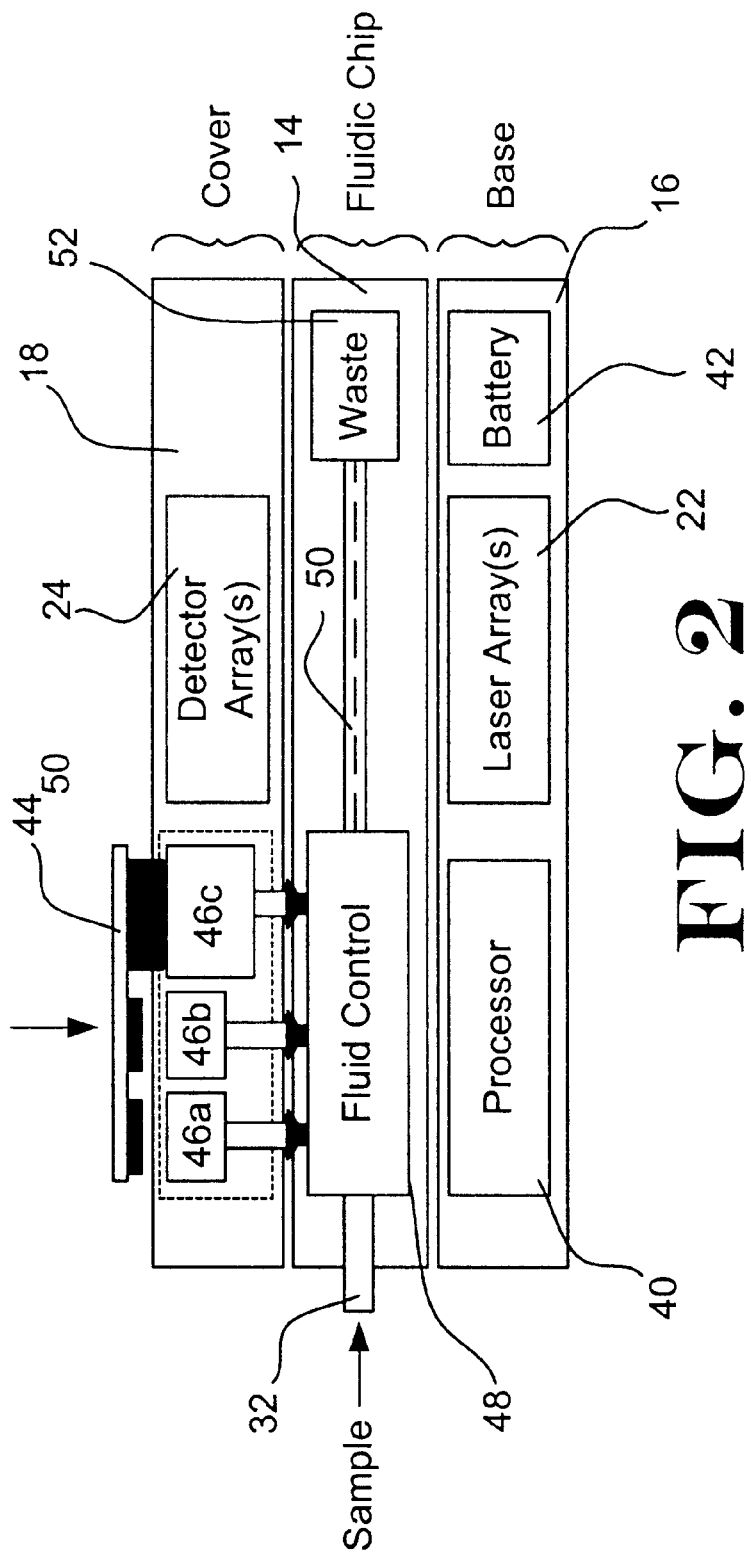
FIG. 2 is a schematic view of the illustrative portable cytometer of FIG. 1.

FIG. 2 is a schematic view of the illustrative portable cytometer of FIG. 1. As above, the base 16 may include an array of light sources 22, associated optics and the necessary control and processing electronics 40 for operation of the cytometer. The base 16 may also include a battery 42 for powering the cytometer. The cover 12 is shown having a manual pressurizing element 44, pressure-chambers 46a, 46b and 46c with control microvalves, and an array of light detectors 24.

The removable cartridge 14 may receive a sample fluid via the sample collector port 32. When pressurized by the cover 18, the removable cartridge 14 performs blood dilution, red cell lysing, and hydrodynamic focusing for core formation in a preferred embodiment. Once formed, the core is provided down a flow stream path 50, which passes the flow stream window 30 of FIG. 1. The array of light sources 22 and associated optics in the base provide light through the core stream via the flow stream window 30. The array of light detectors receive scattered and non-scattered light from the core, also via the flow stream window 30. The controller or processor 40 receives output signals from the array of detectors, and differentiates and counts selected white blood cells that are present in the core stream.

Figure 3:
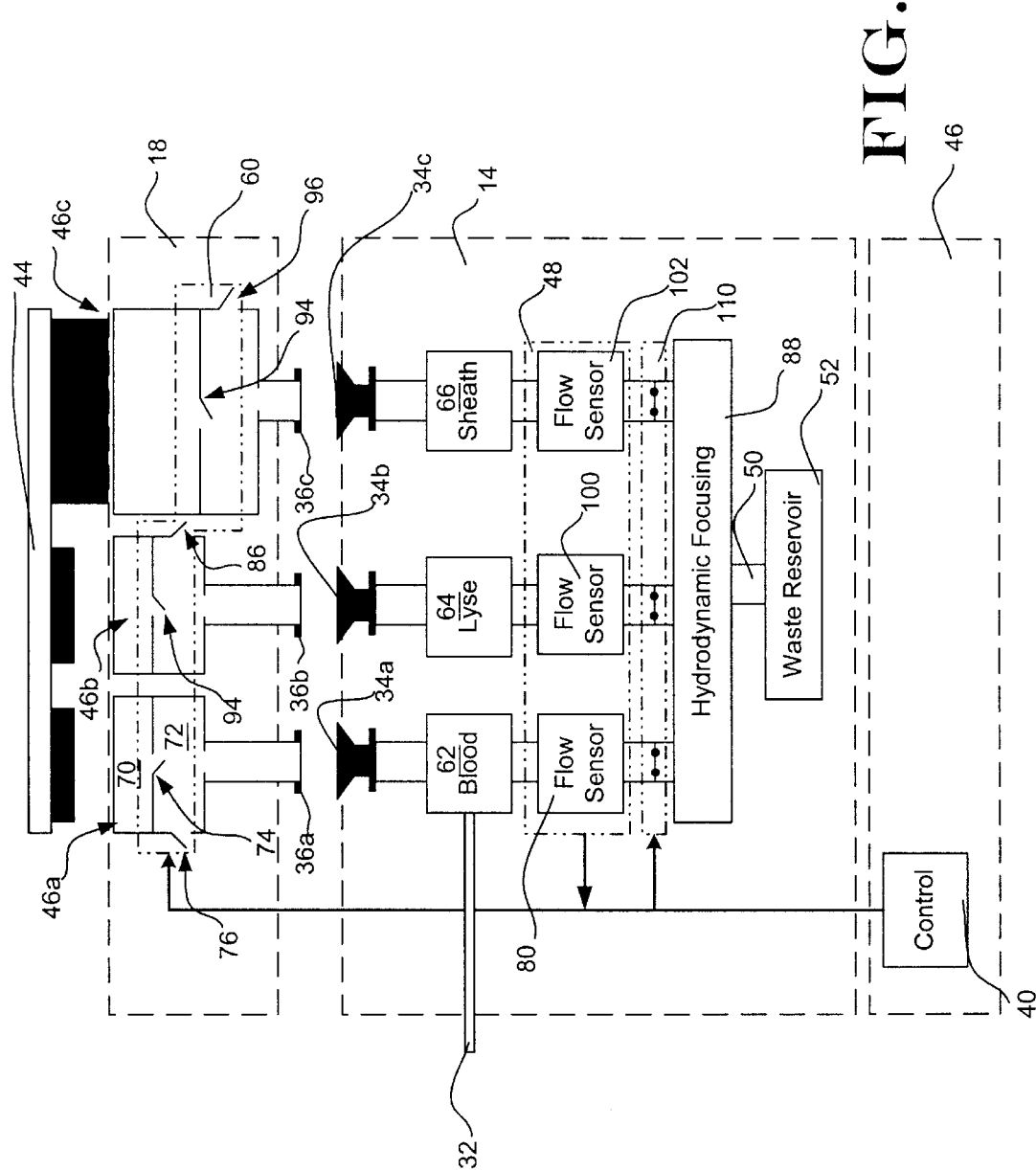
FIG. 3 is a more detailed schematic diagram showing the portable cytometer of FIG. 2 with the cover not yet depressed.
Figure 4:
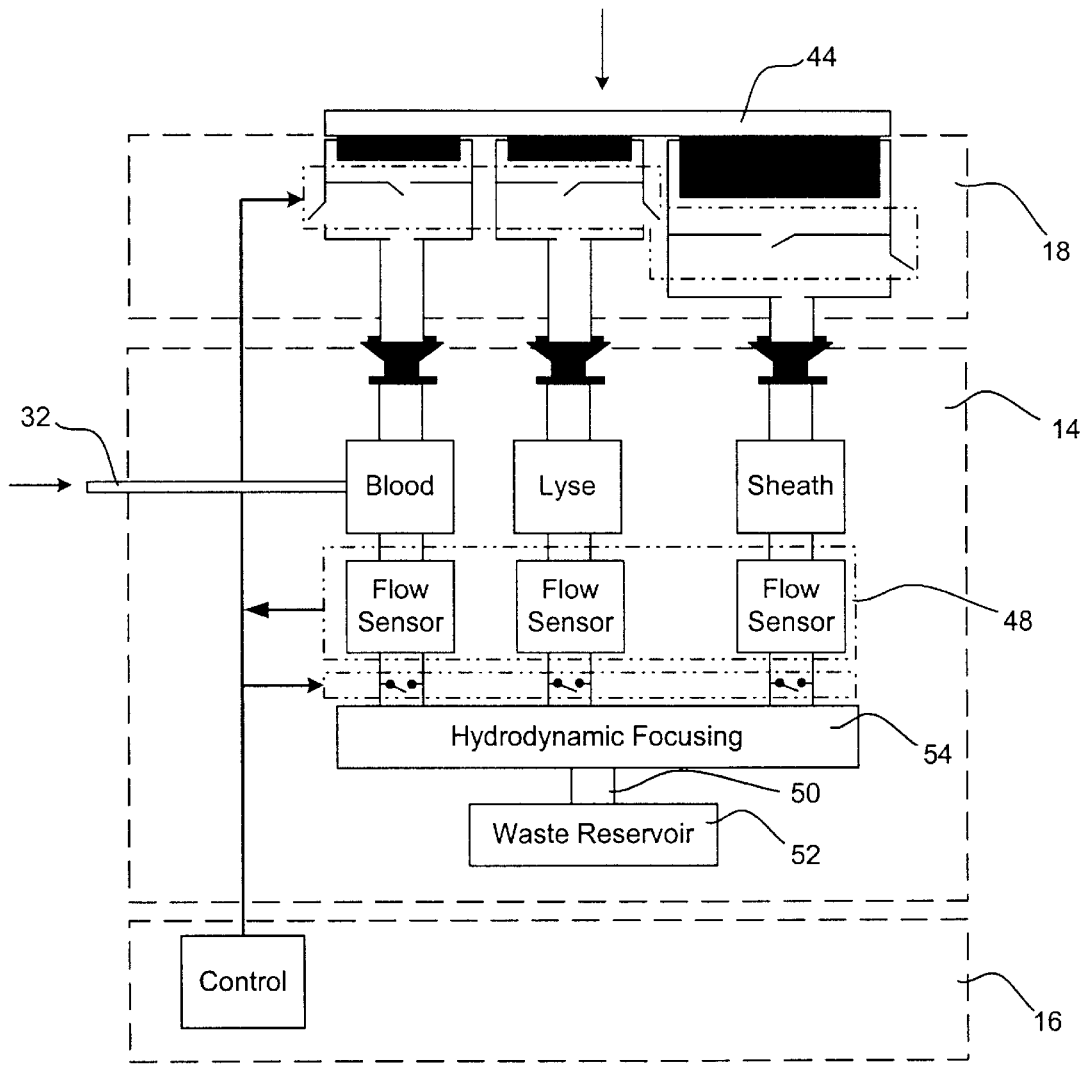
FIG. 4 is a more detailed schematic diagram showing the portable cytometer of FIG. 2 with the cover depressed.

FIG. 3 is a more detailed schematic diagram showing the portable cytometer of FIG. 2 with the cover 18 not yet depressed. FIG. 4 is a more detailed schematic diagram showing the portable cytometer of FIG. 2 with the cover depressed. The cover 18 is shown having a manual pressurizing element 44, pressure-chambers 46a, 46b and 46c, and control microvalves generally shown at 60. The array of light sources and detectors are not shown in these Figures.

There are three pressure chambers 46a, 46b and 46c, one for each fluid to be pressurized. In the illustrative embodiment, pressure chamber 46a provides pressure to a blood sample reservoir 62, pressure chamber 46b provides pressure to a lyse reservoir 64, and pressure chamber 46c provides pressure to a sheath reservoir 66. The size and shape of each pressure chamber 46a, 46b and 46c may be tailored to provide the desired pressure characteristics to the corresponding fluid.

Pressure chamber 46a includes a first pressure chamber 70 and a second pressure chamber 72. A first valve 74 is provided between the first pressure chamber 70 and the second pressure chamber 72 for controllably releasing the pressure in the first pressure chamber 70 to a second pressure chamber 72. A second valve 76, in fluid communication with the second pressure chamber 72, controllably vents the pressure in the second pressure chamber 72. Each valve is preferably an array of electrostatically actuated microvalves that are individually addressable and controllable, as described in, for example, co-pending U.S. patent application Ser. No. 09/404,560, entitled "ADDRESSABLE VALVE ARRAYS FOR PROPORTIONAL PRESSURE OR FLOW CONTROL", and incorporated herein by reference. Pressure chambers 46b and 46c include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 has pressure receiving ports 34a, 34b, and 34c for receiving the controlled pressures from the cover 18. The controlled pressures are provided to the blood reservoir 62, lyse reservoir 64 and sheath reservoir 66, as shown. The lyse reservoir 64 and sheath reservoir 66 are preferably filled before the removable cartridge 14 is shipped for use, while the blood reservoir 62 is filled from sample collector port 32. A blood sample may be provided to the sample collector port 32, and through capillary action, the blood sample is sucked into the blood reservoir 62. Once the blood sample is in the blood reservoir 62, the cover 18 may be closed and the system may be pressurized.

A flow sensor is provided in-line with each fluid prior to hydrodynamic focusing. Each flow sensor 80, 100 and 102 measures the velocity of the corresponding fluid. The flow sensors are preferably thermal anemometer type flow sensors, and more preferably microbridge type flow sensor. Microbridge flow sensors are described in, for example, U.S. Pat. Nos. 4,478,076, 4,478,077, 4,501,144, 4,651,564, 4,683,159, and 5,050,429, all of which are incorporated herein by reference. An output signal from each flow sensor 80, 100 and 102 is provided to controller or processor 40.

The controller or processor 40 opens the first valve 74 when the velocity of the blood sample drops below a first predetermined value and opens the second valve 76 when the velocity of the blood sample increases above a second predetermined value. Valves 84, 86, 94 and 96 operate in a similar manner to control the velocities of the lyse and sheath fluids.

During operation, and to pressurize the system, the manual pressurizing element 44 is depressed. In the example shown, the manual pressurizing element 44 includes three plungers, with each plunger received within a corresponding one of the first pressure chambers. The plungers create a relatively high non-precision pressure in the first pressure chambers. Lower, controlled pressures are built in the secondary chambers by opening the first valves 70, 84 and 94, which produce a controllable leak into the secondary chambers. If too much pressure builds up in the secondary pressure chambers, the corresponding vent valves 76, 86 and 96 are opened to relieve the pressure.

When closing the cover 18, the normally open first valves 74, 84 and 94 are closed while the vent valves 76, 86 and 96 are open. When a predetermined pressure P is achieved in the first pressure chambers, the vent valves 76, 86 and 96 are closed, and the first valves 74, 84 and 94 are opened to build a lower pressure P' in the secondary pressure chambers. The controlled pressure in the secondary pressure chambers provide the necessary pressures to the fluidic circuit of the removable cartridge 14 to produce fluid flow for the blood, lyse and sheath. The velocity of the fluid flow is then measured by the downstream flow sensors 80, 100 and 102. Each flow sensor provides an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another embodiment, downstream valves 110 are opened by mechanical action when the cover is closed.

Figure 5:
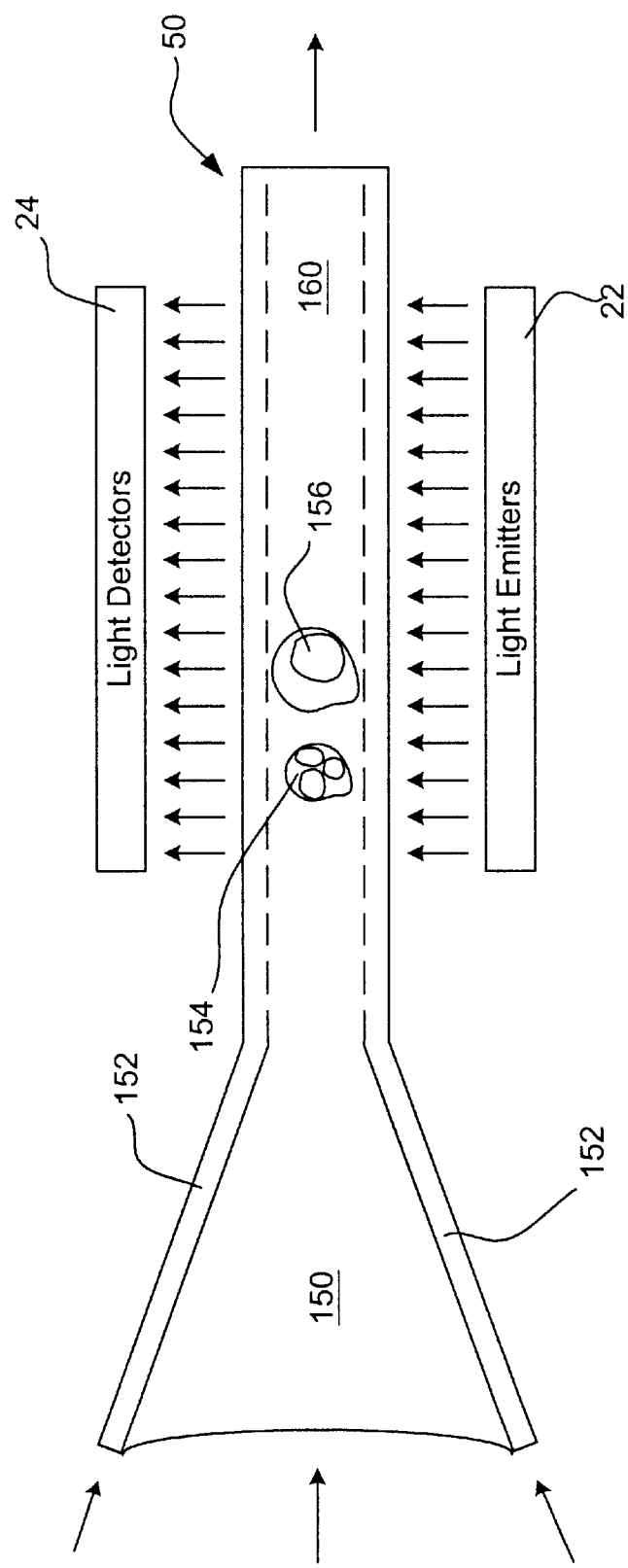
FIG. 5 is a schematic diagram showing the formation of a flow stream by the hydrodynamic focusing block 88 of FIG. 3.

FIG. 5 is a schematic diagram showing the formation of a flow stream and core by the hydrodynamic focusing block 88 of FIG. 3. The hydrodynamic focusing block 88 receives blood, lyse and sheath at controlled velocities from the fluid driver. The blood is mixed with the lyse, causing the red blood cells to be removed. This is often referred to as red cell lysing. The remaining white blood cells are provided down a central lumen 150, which is surrounded by sheath fluid to produce a flow stream 50. The flow stream 50 includes a core stream 160 surrounded by the sheath fluid 152. The dimensions of the channel are reduced as shown so that the blood cells 154 and 156 are in single file. The velocity of the sheath fluid is preferably about 9 times that of the core stream 160. However, the velocity of the sheath fluid and core stream 160 preferably remain sufficiently low to maintain laminar flow in the flow channel.

Light emitters 22 and associated optics are preferably provided adjacent one side of the flow stream 50. Light detectors 24 are provided on another side of the flow stream 50 for receiving the light from the light emitters 22 via the flow stream 50. The output signals from the light detectors 24 are provided to controller or processor 40, wherein they are analyzed to identify and/or count selected white blood cells in the core stream 160. In a preferred embodiment, the blood cells 154 and 156 are white blood cells. In other preferred embodiments, the blood cells may include neutrophils and/or lymphocytes.

FIG. 6 is a diagram showing an illustrative embodiment of the present invention. A lens array 200 is positioned between a light source array 202 and flow channel 50. Each lens in the lens array 200 may be a microlens. The microlenses may be any type of lens including, for example, refractive lenses, diffractive lenses, etc. An annular detector 210, with a center zone 212 and outer zones 214a, 214b, 214c and 214d, is positioned on the opposite side of the flow channel 50 from the light source array 202. A first lens 200a is positioned relative a first light source 202a such that the central focal axis 206a of the lens 200a is offset by a distance "$d_1$" from the light source central axis 204a. A second lens 200b is positioned relative a second light source 202b such that the central focal axis 206b of the lens 200b is offset by a distance "$d_2$" from the light source central axis 204b. The offset distances between the central focal axis of each lens and the corresponding light source central axis preferably changes across the array such that the light rays emitted by each light source is focused onto a common point or region 222 on the annular detector 210. As shown in FIG. 6, the common focal point 222 may appear on the annular detector 210 at or about the center of the central zone 212.

Because the lens array 200 and the light source array 202 are adapted to focus the light rays onto a common point or region 222, no beam shaping optics may be required on the detector side. This may reduce the complexity and cost of the device. Furthermore, particles that pass through the flow channel 50 may produce a simple rotationally symmetric scattering signature, which can be much easier to process at the detector than non-rotationally symmetric scattering signatures.

The light source array 202 is preferably an array of lasers such as Vertical Cavity Surface Emitting Lasers (VCSEL) fabricated on a common substrate. Because of their vertical emission, VCSELs are ideally suited for packaging in compact instruments such as a portable cytometer. Preferably, the VCSELs are "red" VCSELs that operate at wavelengths that are less than the conventional 850 nm, and more preferably in the 670 nm to 780 nm range. Red VCSELs may have a wavelength, power and polarization characteristic that is ideally suited for scatter measurements. Other light sources may be used including, for example, Light Emitting Diodes (LEDs) or any other type of light source.

FIG. 7 is a frontal view of the annular detector 210 shown in FIG. 6. The illustrative annular detector has several zones, including a central zone 212 and several annular shaped outer zones 214a–d. The first zone 214a, which is located just outside of the central zone 212, may be an annular shaped light detector used for detecting forward angle scattering (FALS) produced by one or more particles in the flow stream. The second zone 214b, which is positioned outside of the first zone 214a, may be an annular shaped light detector used for detecting the small angle scattering (SALS) produced by one or more particles in the flow stream. Other annular shaped light detectors 214c and 214d may be positioned outside of the central detector 212 and the first two annular shaped outer detectors 214a and 214b to detect other scatter angles, as desired.

FIG. 8 is a schematic diagram showing a linear array of light sources 22 (indicated by "+" signs) positioned along an axis that is angularly offset by about ninety degrees relative to the central axis of flow of a flow channel 50. FIG. 8 also shows a single annular shaped zoned detector 210 positioned on the opposite side of the flow channel 50. In a preferred embodiment, the light sources 22 are designed with lenses as shown in FIG. 6 so that the light emitted from the array of light sources 22 will have a common focal point or region on the central ring 212 of the detector 210. Preferably, the array of light sources 22 are positioned and spaced to provide a substantially constant light intensity across the width of the flow channel 50.

Using a linear array of lasers offers a number of important advantages over the single light source configuration. For example, a linear array of lasers may be used to determine the lateral alignment of the path of the particles in the core steam. One source of uncertainty in the alignment of the particle stream is the width of the core flow, which leads to statistical fluctuations in the particle path position. These fluctuations can be determined from analysis of the detector data and can be used by the controller or processor 40 (see FIG. 2) to adjust the valves of the fluid driver in order to change the relative pressures that are applied to the sample fluid and the supporting fluids to change the alignment of the selected particles in the flow stream.

To determine the lateral alignment of the particles in the fluid stream 50, the particles pass through the light produced by the linear array of VCSELs. The particles produce a different scatter profile at the detector when the cells are not properly aligned. The relative strengths of the signals at the detector 210 can be used by the controller or processor 40 to determine when the particle path is centered in the flow stream.

FIG. 9 is a schematic diagram showing two linear arrays of light sources, each positioned along an axis that is angularly offset by about ninety degrees relative to the central axis of flow of a flow channel. Each array of light sources has an annular zoned detector positioned on the opposite side of the flow stream. More specifically, a first flow sensor 300 has an array of light sources 22 (indicated as "+" signs) and an annular shaped detector 210 having a center ring 212 and outer rings 214a–d. A second flow sensor 302, which is located either upstream or downstream of the first flow sensor 300, includes an array of light sources 322 (indicated as "+" signs) and an annular shaped detector 310. In the illustrative embodiment, the annular shaped detector 310 of the second flow sensor 302 only has a center ring or region 212.

In preferred embodiments, the first flow sensor 300 is used to measure, for example, the FALS and SALS produced by one or more particles in the flow stream 50. The first flow sensor 300 may also be used to determine the lateral alignment of the path of the particles in the core stream. The second flow sensor 302 is used in conjunction with first flow sensor 300 to measure the velocity of the particles passing through flow channel 50.

To determine the velocity of each particle, the system may measure the time required for each particle to pass between the first detector 210 and the second detector 310. For example, and with reference to FIG. 9, a particle may pass detector 210 and then detector 310. By measuring the time required for the particle to travel from detector 210 to detector 310, and by knowing the distance from detector 210 to detector 310, the controller or processor 40 can calculate the velocity of the particle in the flow stream. This would be an approximate velocity measurement. This is often referred to as a time-of-flight measurement. Once the velocity is known, the time of travel through the light beam of the first or second flow sensors 300 or 310 (a few microseconds) may provide a measure of particle length and size.

It is contemplated that the particle velocity can also be used to help control the fluid driver. To reduce the size, cost and complexity of the present invention, the replaceable cartridge of FIG. 1 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed above can be used by the controller or processor 40 to adjust the controlled pressures applied to the blood, lyse and sheath fluid streams such that the particles in the core stream have a relatively constant velocity.

To further evaluate the particle size, it is contemplated that laser beams may be focused both along the particle path and across the particle path. Additionally, multiple samples across the particle may be analyzed for texture features, to correlate morphological features to other particle types. This may provide multiple parameters about particle size that may help separate particle types from one another.

FIG. 10 is a schematic diagram showing two linear arrays of light sources along an axis that is angularly offset by less than ninety degrees relative to the central axis of the flow channel 50. This embodiment is similar to that shown in FIG. 9, but each of the flow sensors 300 and 302 are rotated relative to the central axis of the flow channel. One advantage of this embodiment is that the effective spacing of the light sources, as viewed by a particle, may be less than that provided by the embodiment of FIG. 9. This may allow a more uniform illumination intensity across the flow channel.

Figure 11:
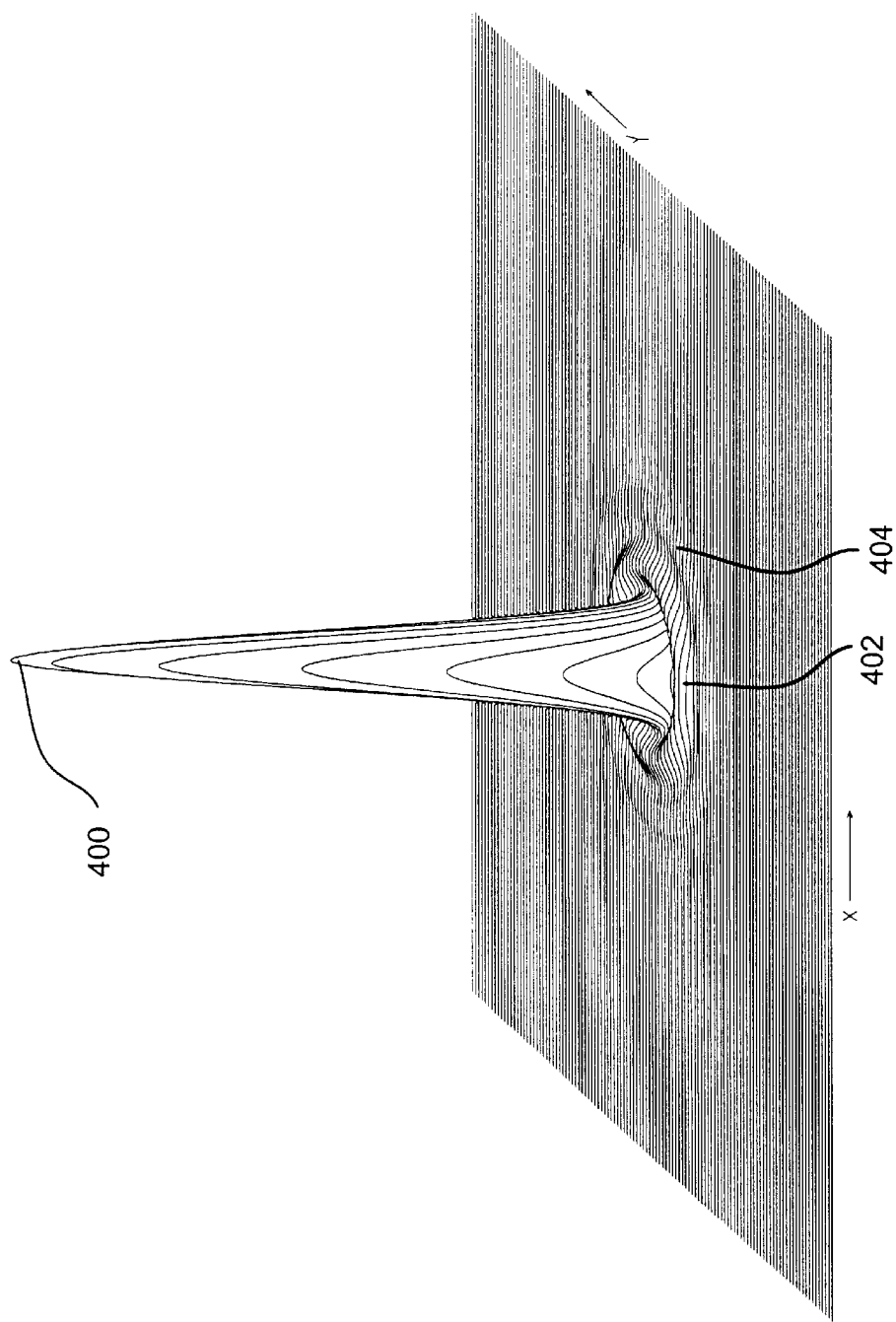
FIG. 11 is an illustrative graph representing the intensity distribution of light striking an annular detector when no particle is present in the flow channel.

FIG. 11 is an illustrative graph representing the intensity distribution of light striking the annular detector 210 of FIG. 6 with no particle in the flow channel 50. This graph shows a classic airy diffraction intensity distribution. Most of the diffraction pattern intensity is concentrated in a central zone, as shown by the center peak 400. A first outer peak 402 and a second outer peak 404 can also be observed from the graph. The first and second outer peaks 402, 404 are of substantially lesser magnitude than the first peak 400, but are large enough to be noted on the graph.

Figure 12:
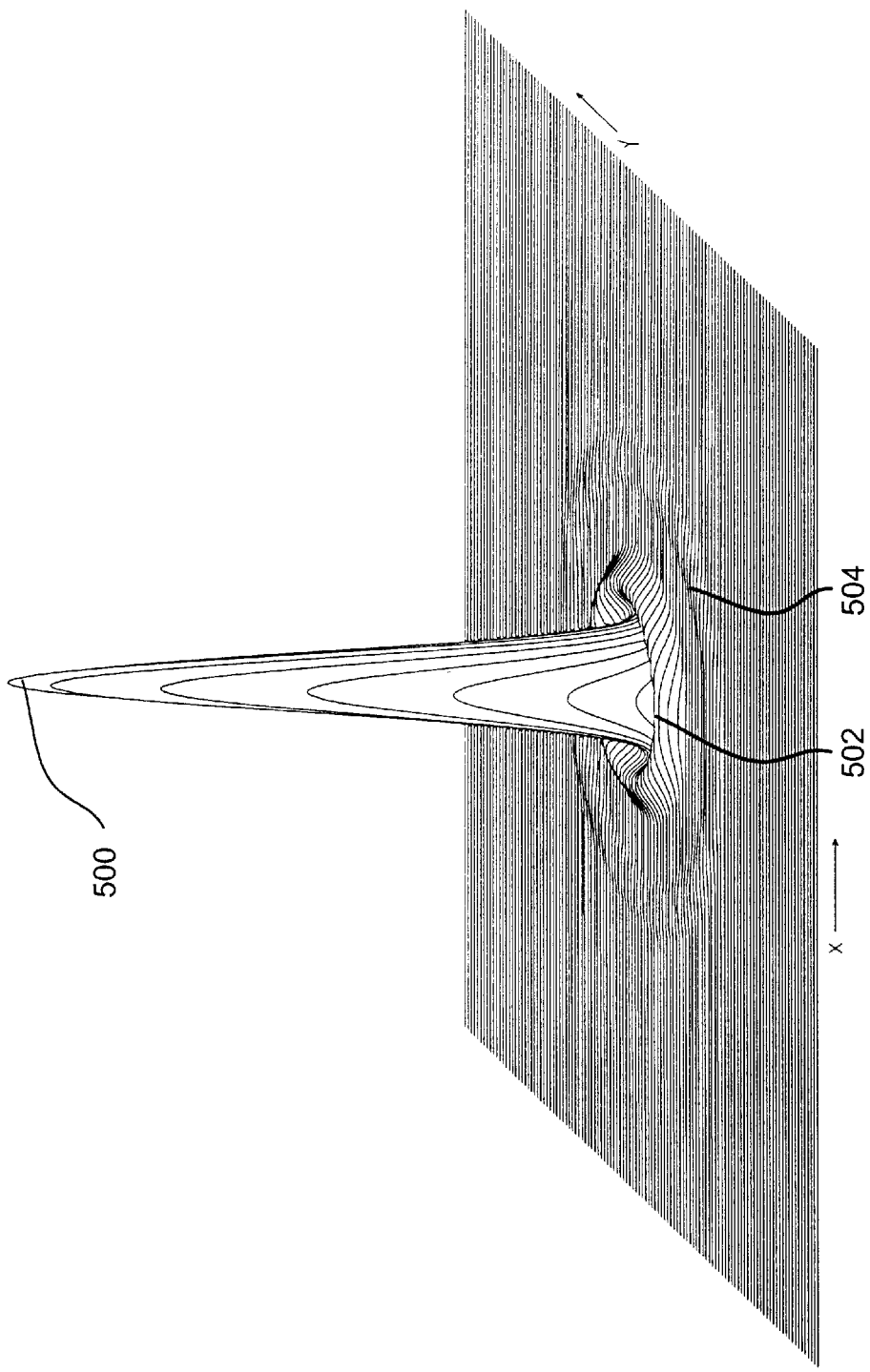
FIG. 12 is an illustrative graph representing the intensity distribution of light striking the annular detector when a particle is present in the flow channel.

FIG. 12 is an illustrative graph representing the intensity distribution of light striking the annular detector 210 of FIG. 6 when a particle is present in the flow channel 50. A central peak 500, a first outer peak 502, and a second outer peak 504 are shown. This graph demonstrates that, while the central peak 500 is similar in magnitude to the central peak 400 shown in FIG. 11, the comparative difference between the central peak 500 and the first outer peak 502 is of different magnitude than the comparative difference between central peak 400 in FIG. 11 and first outer peak 402 of FIG. 11. FIG. 12 also demonstrates that the second outer peak 504 is relatively farther away from the central peak 500 than the second outer peak 404 is from the center peak 400 of FIG. 11. These graphs also demonstrate the rotational symmetry of the light scatter signature that occurs in the present invention.

The graphs in FIGS. 11 and 12 represent data that, in preferred embodiments, is collected by the annular detector 210 of FIG. 6. This data is then sent to a processor 40 (FIG. 2) to perform various data processing functions. Possible functions include, but are not limited to, flow alignment, blood cell counting, identification of foreign objects, blood cell identification, flow speed, and identification of neutrophils and/or lymphocytes white blood cells. In a preferred embodiment, the ratio of annular zone signal strengths that are detected by the various zones in the detector 210 can be used to determine whether a blood cell is present and/or the type of blood cell present.

Having thus described the preferred embodiments of the present invention, those of skill in the art will readily appreciate that the teachings found herein may be applied to yet other embodiments within the scope of the claims hereto attached.

What is claimed is:

1. An optical detection system for analyzing characteristics of a flow stream, the flow stream having a central axis along the direction of flow, the optical detection system comprising:

two or more spaced light sources positioned on a first side of the flow stream for providing light through the flow stream;

lens means positioned on the first side of the flow stream for focusing the light from each of the two or more light sources to a common focal point located on a second opposite side of the flow stream;

light receiving means for receiving the light from the two or more light sources, and for providing at least one signal in response thereto, at least a portion of the light receiving means located at the common focal point of the lens means; and processing means for receiving the at least one signal from the light receiving means and for using the at least one signal for analyzing the characteristics of the flow stream.

2. An optical detection system according to claim 1, wherein each of the two or more light sources are positioned laterally at different distances from the central axis of the flow stream.

3. An optical detection system according to claim 1, wherein each of the two or more light sources are Vertical Cavity Surface Emitting Lasers (VCSELs).

4. An optical detection system according to claim 3, wherein the VCSELs operate in the red spectrum.

5. An optical detection system according to claim 1, wherein each of the two or more light sources are Light Emitting Diodes (LEDs).

6. An optical detection system according to claim 1, wherein the two or more light sources are an array of light sources.

7. An optical detection system according to claim 1, wherein the lens means includes two or more microlenses, one for each of the two or more light sources.

8. An optical detection system according to claim 7, wherein each microlens is laterally offset relative to the corresponding light source so that the light provided by each light source is focused onto the common focal point.

9. An optical detection system according to claim 1, wherein the light receiving means includes a centrally located light detector positioned at the common focal point.

10. An optical detection system according to claim 9, wherein the light receiving means includes a first annular shaped light detector positioned around the centrally located light detector.

11. An optical detection system according to claim 10, wherein the first annular shaped light detector is used for detecting the scattering produced by one or more particles in the flow stream.

12. An optical detection system according to claim 11, wherein the one or more particles include white blood cells.

13. An optical detection system according to claim 12, wherein the white blood cells include neutrophils and/or lymphocytes.

14. An optical detection system according to claim 10, wherein the light receiving means includes a second annular shaped light detector positioned around the first annular shaped light detector.

15. An optical detection system according to claim 14, wherein the second annular shaped light detector is used for detecting the scattering produced by one or more particles in the flow stream.

16. An optical detection system according to claim 15, wherein the one or more particles include white blood cells.

17. An optical detection system according to claim 16, wherein the white blood cells include neutrophils and/or lymphocytes.

18. An optical detection system according to claim 14, wherein the light receiving means includes at least one other annular shaped light detector positioned around the second annular shaped light detector.

19. An optical detection system according to claim 1, wherein the two or more spaced light sources are positioned along a light source axis that is angularly offset relative to the central axis of flow of the flow stream.

20. An optical detection system according to claim 19, wherein the light source axis is angularly offset by about 90 degrees relative to the central axis of flow of the flow stream.

21. An optical detection system according to claim 19, wherein the light source axis is angularly offset by less than 90 degrees relative to the central axis of flow of the flow stream.

22. An optical detection system according to claim 1, wherein the two or more spaced light sources collectively provide a substantially constant light intensity across the flow stream.

23. An optical detection system according to claim 1, wherein the light that is provided through the flow stream is used for determining the velocity of one or more particles in the flow stream.

24. An optical detection system according to claim 1, wherein the light that is provided through the flow stream is used for determining the size of one or more particles in the flow stream.

25. An optical detection system according to claim 1, wherein the two or more light sources include a first set of light sources positioned along a first light source axis and a second set of light sources positioned along a second light source axis, wherein the second light source axis is located downstream or upstream of the first light source axis.

26. An optical detection system according to claim 25, wherein light receiving means includes a first detector and a second detector.

27. An optical detection system according to claim 26, wherein the lens means includes a first set of microlenses associated with the first set of light sources and a second set of microlenses associated with the second set of light sources.

28. An optical detection system according to claim 27, wherein the first set of microlenses are adapted to focus the light from the first set of light sources to a first common focal point, and the second set of microlenses are adapted to focus the light from the second set of light sources to a second common focal point.

29. An optical detection system according to claim 28, wherein the first detector of the light receiving means has a centrally located light detector positioned at the first common focal point and the second detector of the light receiving means has a centrally located light detector positioned at the second common focal point.

30. An optical detection system according to claim 29, wherein the first detector includes at least one annular shaped light detector positioned around the centrally located light detector.

31. An optical detection system according to claim 29, wherein the second detector includes at least one annular shaped light detector positioned around the centrally located light detector.

32. An optical detection system according to claim 29, wherein the second detector does not include an annular shaped light detector around the centrally located light detector.

33. An optical detection system according to claim 29, wherein the first set of light sources and the first detector are used to detect the alignment of the flow of one or more particles relative to the central axis of the flow stream.

34. An optical detection system according to claim 29, wherein the first set of light sources and the first detector are used to detect the speed of one or more particles in the flow stream.

35. An optical detection system according to claim 29, wherein the first set of light sources and the first detector are used to detect the size of one or more particles in the flow stream.

36. An optical detection system according to claim 29, wherein the second set of light sources and the second detector are used in conjunction with the second set of light sources and the second detector to determine the speed of one or more particles in the flow stream.

37. A method for determining the position of one or more particles in a flow stream relative to a central axis of the flow stream, the method comprising:

activating two or more light sources positioned on a first side of the flow stream for providing light through the flow stream;

focusing the light from each of the two or more light sources to a common focal point located on a second opposite side of the flow stream;

monitoring an output response of a detector, wherein at least a portion of the detector is positioned at the common focal point, the output response providing an indication of the position of the one or more particles in the flow stream; and determining the position of the one or more particles in the flow stream by examining the output response of the detector.

38. A method for determining the velocity of one or more particles in a flow stream, the method comprising:

activating two or more upstream light sources at an upstream position of the flow stream to provide light through the flow stream;

focusing the light from each of the at least two or more upstream light sources to a first common focal point behind the flow stream;

monitoring an output response of an upstream detector that receives the light from the two or more upstream light sources;

activating two or more downstream light sources at a downstream position of the flow stream to provide light through the flow stream;

focusing the light from each of the at least two or more downstream light sources to a second common focal point behind the flow stream;

monitoring an output response of a downstream detector that receives the light from the two or more downstream light sources;

detecting a change in the output response of the at least one upstream detector when a particle passes between the at least two upstream light sources and the upstream detector;

detecting a change in the output response of the downstream detector when the same particle passes between the at least two downstream light sources and the downstream detector; and determining a time lag between the change in output response of the upstream detector and the change in output response of the downstream detector, the time lag being related to the speed of the particle.

* * * * *